United States Patent [19]

Kerschgens

[11] Patent Number: 4,595,838

[45] Date of Patent: Jun. 17, 1986

[54] IRRADIATION DEVICE

[76] Inventor: Johann J. Kerschgens, Prinz-Ludwig-Strasse 5, D-8918 Diessen am Ammersee, Fed. Rep. of Germany

[21] Appl. No.: 608,940

[22] PCT Filed: Aug. 29, 1983

[86] PCT No.: PCT/EP83/00227

§ 371 Date: Apr. 20, 1984

§ 102(e) Date: Apr. 20, 1984

[87] PCT Pub. No.: WO84/00897

PCT Pub. Date: Mar. 15, 1984

[30] Foreign Application Priority Data

Sep. 1, 1982 [DE] Fed. Rep. of Germany ....... 3232537
Dec. 9, 1982 [DE] Fed. Rep. of Germany ....... 3245654
Dec. 9, 1982 [DE] Fed. Rep. of Germany ....... 3245655
Jun. 18, 1983 [DE] Fed. Rep. of Germany ... 8317832[U]

[51] Int. Cl.[4] .............................................. A61N 5/06
[52] U.S. Cl. ............................ 250/504 R; 250/504 H
[58] Field of Search ............... 250/504 H, 504 R, 503, 250/493

[56] References Cited

U.S. PATENT DOCUMENTS 1,579,513 5/1925 Cameron .................... 250/504 R

FOREIGN PATENT DOCUMENTS 206108 11/1959 Austria ........................ 250/493.1
1464661 2/1969 Fed. Rep. of Germany .
2714724 10/1978 Fed. Rep. of Germany .
2823615 12/1979 Fed. Rep. of Germany .
2832143 1/1980 Fed. Rep. of Germany .
2841112 4/1980 Fed. Rep. of Germany .
2906512 8/1980 Fed. Rep. of Germany .

Primary Examiner—Alfred E. Smith
Assistant Examiner—Jack I. Berman
Attorney, Agent, or Firm—Michael J. Striker

[57] ABSTRACT

A radiating device consisting of a blower (140) and a radiation source (38) which emits ultra violet radiation (UV-radiation) being connected with a voltage-dropping impedance and with an AC-power source, whereby the radiation source cooperates with an air flow which is generated by the blower, in particular a hair dryer (141). The voltage dropping impedance is mainly capacitive and the radiation source (33) is arranged in the air flow of the blower, whereby the air flow cools the radiation source in such a manner that that the instantaneous value of its restriking voltage ≦ to the instantaneous value of the line voltage.

71 Claims, 16 Drawing Figures

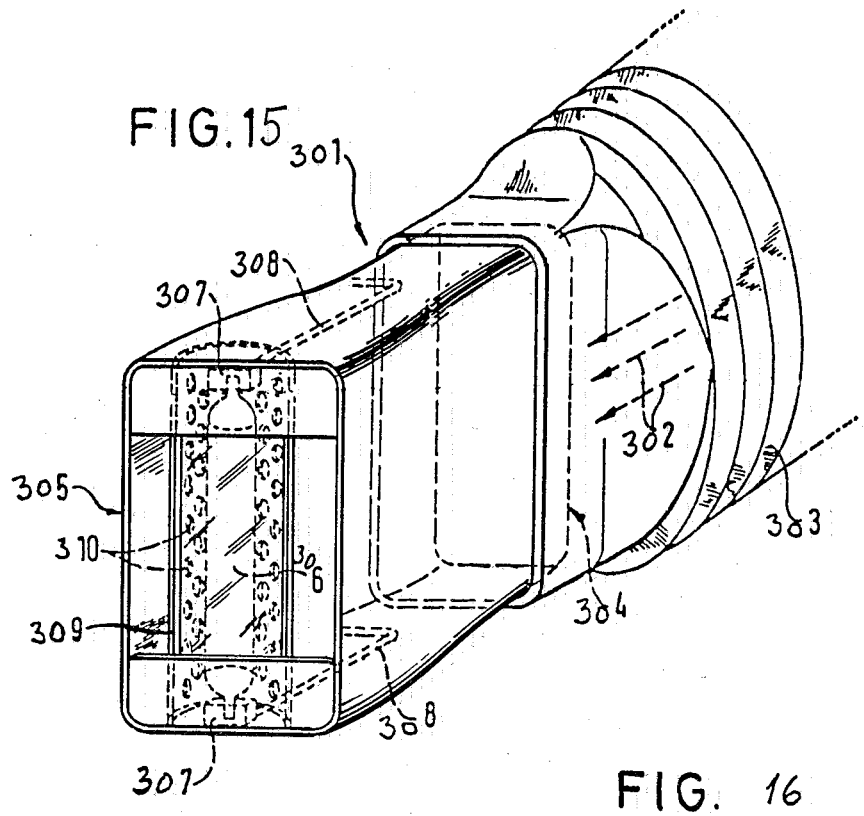
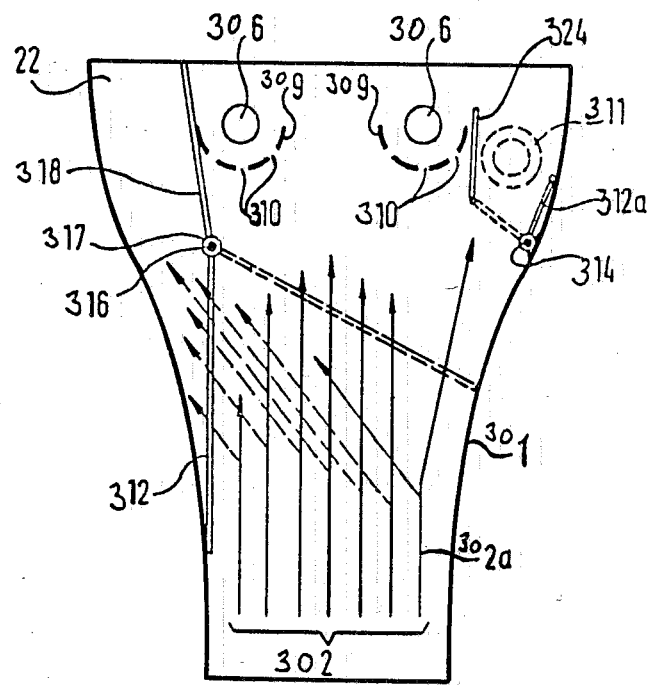

IRRADIATION DEVICE

BACKGROUND OF THE INVENTION

This invention relates to an irradiation device, this being made up of a blower and a source of radiation that emits ultraviolet radiation (UV radiation) and which is connected to an AC-power source through a dropping resistor; the radiation source works in conjunction with the flow of air that is generated by the blower.

Irradiation devices that incorporate mercury vapour lamps that emit UV radiation and electrically heated elements to emit IR radiation are already familiar. The ultraviolet rays from the mercury vapour lamps are used to irradiate the skin in order to achieve therapeutic and cosmetic effects, and/or to increase the body's powers of resistance. According to their wave lengths, ultraviolet radiation is classified into UV-A, UV-B and UV-C radiation. UV-A rays have a wave length of 315–400 nm. UV-B rays are of a wave length of 280–350 nm. and UV-C rays lie in the range between 200 and 280 nm. The effect of UV radiation is very varied. As an example, human skin reacts to UV-B and UV-A rays by browning. Ozone can be produced with UV-C radiation; in addition, it destroys micro-organisms such as bacteria, viruses, spores, yeasts, algae, protozoa, and mildew. Ultraviolet rays bring about photo-biological effects in human skin. Shortwave UV radiation brings about the so-called UV-erythema as a result of which the skin becomes brown after a few days (indirect pigmentation). On the other hand, large doses in the longwave UV-range cause direct pigmentation that can be achieved without erythema. The maximum skin sensitivity for direct pigmentation is at a wavelength of 360 nm.

In addition to the effect of UV radiation for browning the skin it has been shown that a stream of air directed at a skin disorder (e.g. psoriasis) in conjunction with UV irradiation leads to an extraordinarily good healing effect and to a rapid alleviation of the disorder.

An irradiation device is familiar in which a hair dryer is used in conjunction with a UV lamp. Since the UV lamp in this familiar device is operated through a DC dropping resistor longer periods of operation will lead to heating of the UV lamp as a result of heat conduction and particularly through thermal radiation. In this regard, it has turned out that the effectiveness of the device diminishes when the UV lamp is used for longer operating periods, and this in turn leads to protracted treatment periods, and furthermore makes it extremely difficult to replicate treatment therapy. Furthermore, it is a disadvantage that the heat that is radiated by the DC dropping resistor also leads to an undesirable heating of the area being treated, which in turn means that the user is inclined to position the radiation device relatively far from the area to be treated, which also reduces the effectiveness of such treatment.

Also familiar is an irradiation device that uses a UV lamp in combination with one or more IR radiators. In most instances a mercury vapour lamp is used as the UV lamp and a resistance heating element is used as the infrared radiator. This heating element also serves as a dropping resistor for the UV lamp. This restricts the UV lamp current and establishes the operating point for the UV lamp. During the operation of the UV lamp the IR radiator (heating element) also heats up since these two components are connected in series. Thus the above-cited disadvantages occur here as well; furthermore, this familiar device does not provide the flow of air that is required for successful treatment.

SUMMARY OF THE INVENTION

Thus it is an object of the present invention to provide an improved irradiation device of the type described in the introduction and which is characterized by a compact, light and inexpensive construction, contains only a few components, suitable for continuous operation, and permits an even treatment effect during the total burning life of the ultraviolet lamp and which, at the same time, can be used relatively close to the area to be treated.

According to the present invention, this task is solved in that the dropping resistor is replaced by a capacitive impedance and the source of radiation arranged in the flow of air generated by the blower, in which regard the airflow cools the source of radiation such that the instantaneous value of its restriking voltage is less than or equal to the instantaneous value of the line voltage.

Advantageous developments of the invention are described by the subclaims.

The invention is based on the knowledge that the operating point of the UV lamp is displaced if it is heated, this also leading to a change in the wave length and power of the UV radiation that is emitted. However, in order to achieve successful treatment it is essential that the UV radiation is made up from only a relatively narrow and specific frequency spectrum of UV radiation. The emission of this desired radiation spectrum is possible with the irradiation device according to the present invention since the dropping resistor for the UV lamp is capacitive and heats up only slightly during operation. However, this means that there is no heating—and thus an associated shift of the operating point—of the adjacent UV lamp as is the case in already familiar irradiation devices. In these already familiar devices, the shift in the operating point leads to a change of the wave length of the UV radiation that is emitted so that the emission of a specific range of wave lengths that is required for successful treatment is not possible. According to the present invention the use of a condenser that heats up only slightly means that the operating point of the UV lamp remains constant even during longer operating times so that a desired wave length spectrum is emitted.

According to a further development of the invention it is provided that the blower is a hair dryer on which a housing that contains the UV lamp can be installed and locked into position. The use of a hair dryer entails the advantage that, on the one hand, the UV assembly (housing with the UV lamp) can be made very small and, on the other—when the UV assembly is removed—the hair dryer can be used as a conventional device for hair drying. The irradiation device according to the present invention thus involves various modes of operation, namely (a) UV-irradiation;
hair drying;
(c) UV-irradiation and hairdrying.

According to a further development of the invention the stream of cooling air from the blower is controlled according to the temperature of the UV lamp. This means that the temperature of the UV lamp can be kept at a specific level at which the lamp will radiate a prescribed UV radiation power and a wave length which represents the optimal radiation for the purpose that is desired.

The use of a condenser as a dropping resistor for the UV lamp is not obvious to the expert since up to now in an arrangement of this kind the UV lamp starts to flicker after a relatively short operating time (a few minutes) and a little after this the UV lamp is extinguished. Thus, according to the present state of knowledge continuous operation is not possible if a condenser is used as a dropping resistor. The reason for the UV lamp being extinguished is as follows: with an increase in operating time the temperature of the UV lamp also increases. A rise in the restriking voltage of the UV lamp is connected with this every time the UV lamp is triggered, which takes place in every half wave of the line voltage, interfering voltages (reactive effects) occur whose frequency is higher than that of the line voltage. This lowers the reactive impedance of the capacitive, and thus frequency dependent, dropping resistor so that the voltage at the UV lamp increases. However, this leads to an increase of the lamp current and to a simultaneous increase in temperature of the UV lamp that in its turn results in an increase of the restriking voltage. Simultaneously with this the interfering frequencies are amplified this once again leads to a further drop in the resistive value of the capacitive dropping resistor. This process builds up until the restriking voltage required by the UV lamp is greater than the available line voltage. A high voltage of this kind cannot however be made available for the UV lamp so that the lamp is extinguished. The invention solves the problem that is associated with this in that the UV lamp is cooled by a stream of air, this preventing an increase of the restriking voltage to an inadmissibly high value, since the restriking voltage of the UV lamp can be influenced by its temperature. This leads to the surprising result that it is possible to achieve protracted operation of a UV lamp with a capacitive dropping resistor ahead of it, without any breakdown.

BRIEF DESCRIPTION OF THE DRAWINGS

FIG. 15 is a perspective view of a particularly useful irradiation device;

FIG. 16 is a perspective view of an irradiation device according to the invention.

DETAILED DESCRIPTION OF THE PREFERRED EMBODIMENTS

Figure 1:
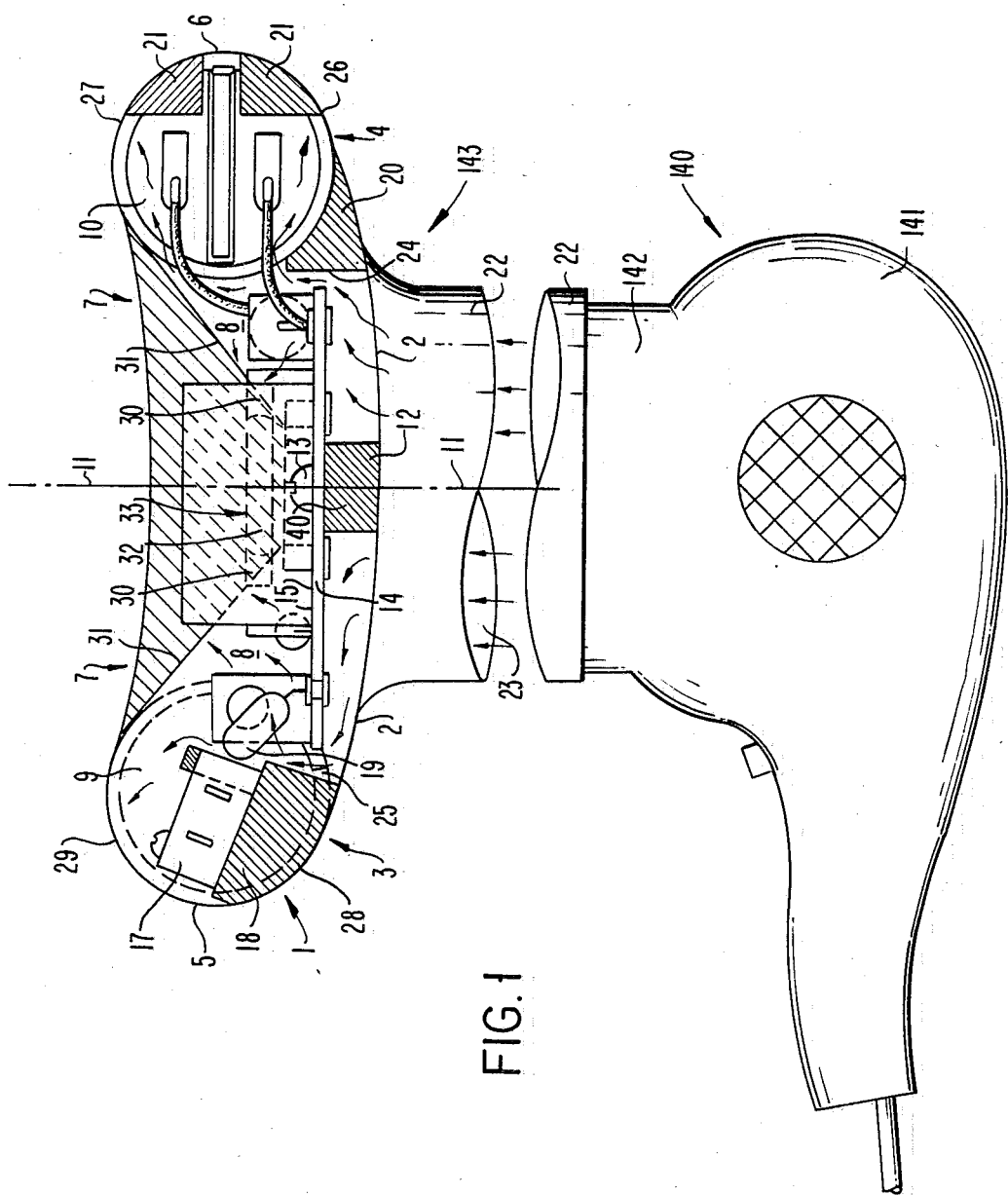
FIG. 1 is a cross-section through the irradiation device according to the invention, this being a partial cut-away drawing.

Viewed from the radiation side, which is to say the top side as is shown in FIG. 1, the irradiation device according to the invention, which is shown in FIG. 1, has a housing with a concave rear wall which, at its outer extremities 3 and 4, becomes partially circular rounded portions 5 and 6. The rounded portions 5 and 6, viewed from the irradiation side, border on a reflector space 7. In the interior 8 of the housing 1 there are at each end and matched to the rounded portions 5 and 6 condensers 9, 10 respectively. Centrally on the longitudinal axis 11 of the housing 1 there is a circuit board attachment 12, a circuit board 14 being secured to this by means of a securing screw 13. The longitudinal axis 11 is perpendicular to the surface 15 of the printed circuit board 14. Various components for a UV lamp 33 that is arranged in the reflector space 7 are set out on the printed circuit board 14. On the left-hand side in FIG. 1 there is a microswitch 17 in front of the condenser 9 and this is secured to a switch mounting 18 that forms part of the housing 1; this microswitch 17 is used to switch the irradiation device on and off. This switching is affected by pressure on a pushbutton for the microswitch 17, this pushbutton being accessible from the outside, but not shown in the illustration. A thermoswitch 19 that is connected to the microswitch 17 monitors the temperature in the interior 8 of the housing 1 and switches the irradiation device off in the event that a preselected temperature, e.g. 80°, is exceeded. Each of the condensers 9, 10 is supported in a mounting 20 and secured by a twist lock 21 (only shown for the condenser 10 in FIG. 1. It is preferred that the mounting 20 be sprung.

A mounting sleeve 22 is connected to the rear wall 2 coaxially to the longitudinal axis 11 and this serves to mount the housing 1 on a blower 140.

According to a further development of the invention the blower 140 is a hairdryer 141 to the air outlet 142 of which the mounting sleeve 22 can be secured by a push-fit. In another version attachment can be by means of a coarse screw thread, or radial securing screws can be provided.

The stream of air that is emitted from the blower 140 is shown by the arrows in FIG. 1 and this first passes through the opening 23 of the mounting sleeve 22 and further on passes through the air channels 24, 25 respectively, left between the printed circuit board 14 and the condensers 9, 10, respectively. A portion of the airflow passes over the condensers 9 and 10 then emerges from the housing 1 through the outlets 26, 27, 28 and 29 that are provided in the vicinity of the condensers 9, 10. This partial airflow thus washes around the condensers 9 and 10. A further partial airflow moves around the UV lamp socket 30 that is mounted on the printed circuit board 14 and then leaves the housing 1 through other air outlets that are not shown in the illustration.

It is foreseen that the walls 31 that surround the reflector space 7 are provided with openings through which a part of the airflow can move thereby cooling the glass bulb 32 of the UV lamp 33 as well as the reflector space 7.

Two cutouts (not shown in the illustrations) can also be provided in the upper portion of the housing 1, these making it possible to solder the lamp connecting wires for the UV lamp 33 into the printed circuit board 14 from above (FIG. 1). The cutouts are covered by the subsequent installation of covers (not shown in the illustrations) for the lamp attachments by means of end caps. The lamp holder and its covers are then so configured that the smallest possible openings to the interior 8 of the housing 1 remain in order to avoid the interior 8 being heated by the UV lamp 33.

Figure 2:
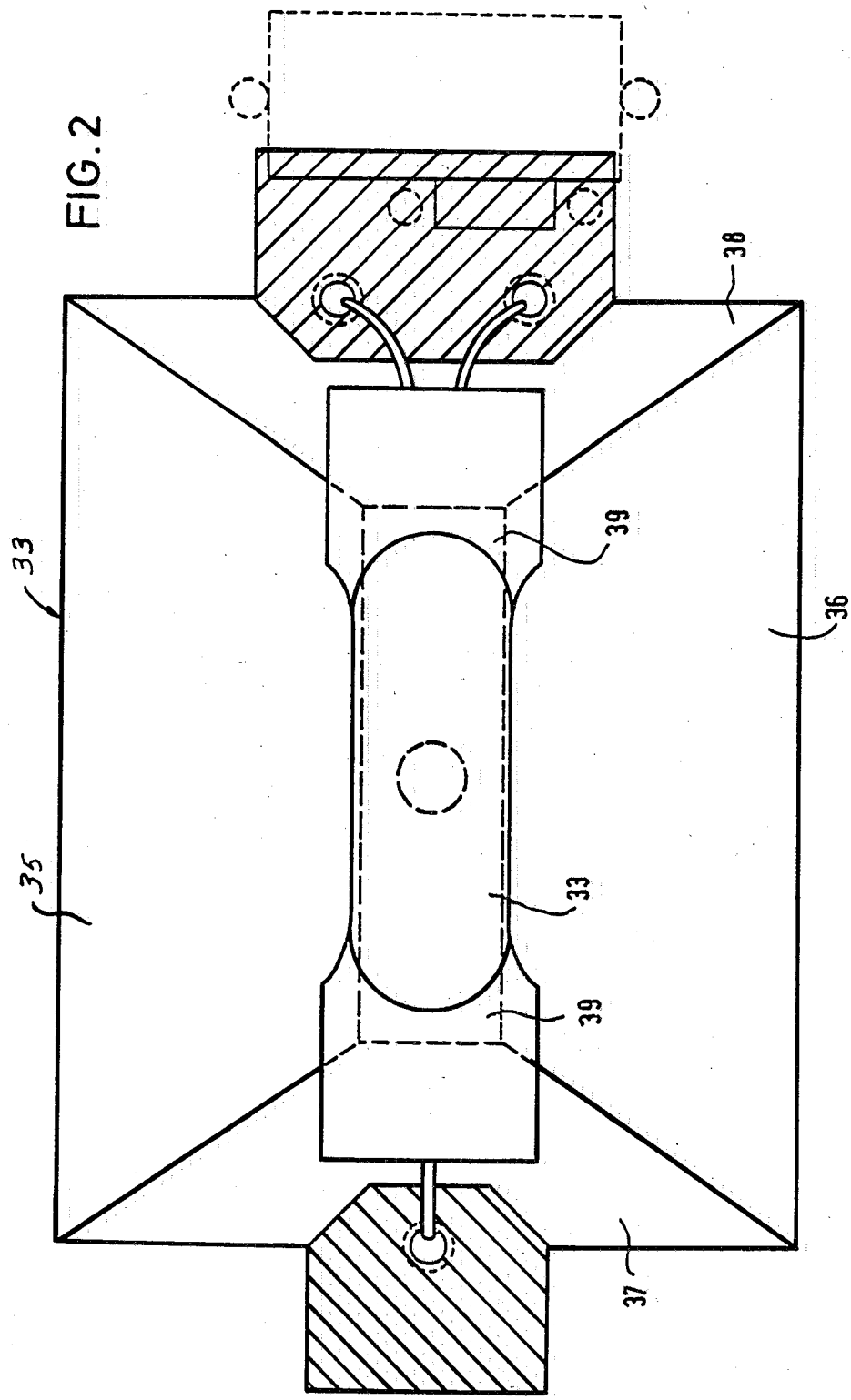
FIG. 2 is a plan view of the device according to FIG. 1.

FIG. 2 shows a plan view of the UV lamp 33 as well as its reflector 34 that is arranged in the reflector space 7, this being in the direction of the object that is to be irradiated. It is preferred that the reflector 34 consists of five flat reflector surfaces 35 to 39 that are so arranged as to provide optimal reflection of the radiation emitted by the UV lamp 33.

The reflector surfaces 35 to 39 are provided with openings through which a part of the air current generated by the blower moves in order to cool the UV lamp.

According to a further version of the invention several UV lamps can be arranged in the reflector space 7.

It can be seen particularly from FIG. 2 that the total reflector surface of the reflectors 34 is available to reflect the UV radiation. This is not the case in familiar irradiation devices for an IR radiator that acts as a dropping resistor is also arranged within the reflector space. This reduces the effect of reflector surface so that the radiation power that is emitted by the UV lamp can in these familiar devices be lower than that in the comparable device according to the present invention.

As a result of the configuration of the reflector 34 with its five reflector surfaces 35 to 39 the object will be irradiated from several directions with diverging light by use of the device according to the invention, so that uneven flat parts or surfaces of the object to be irradiated, e.g. the surfaces of the face of the person to be irradiated, will be irradiated equally. Regardless of the various distances to the device each part of the body receives an almost equal radiation dose; furthermore, compared to the parabolic reflectors that are used in familiar devices, the reflector according to the invention, with its flat surfaces, is less costly and is simpler to produce.

According to a further development of the invention it has been foreseen that in order to suppress specific areas of the spectrum of UV radiation and/or longwave visible radiation and/or IR radiation there are additional filter devices arranged in the reflector space 7. Since the spectral division of the radiation that covers the body to be irradiated is affected to a very great extent by the material used on the surface layer of the reflector it is preferred that material that provides good reflection of UV-A radiation be used for this purpose. Materials of this type are for example yellow eloxated aluminum (anodized aluminum), highly polished stainless steel with a high chromium content, or chromium. In order to be able to arrive at some idea concerning the dimensions of the exemplary version described, several dimensions should be quoted. The radius of the rounded portions 5 and 6 amounts to approximately 140 mm. The distance between the underside of the printed circuit board 14 and the rear wall of the housing 2 is approximately 6 mm in the area of the longitudinal axis 11. The distance between the surface 15 of the printed circuit board 14 and the reflector 34 should amount to approximately 3 mm because of the attachment screw 13 and because of wiring problems, this distance being indicated by the number 40 in FIG. 1. The irradiation device according to the present invention weighs approximately 250–300 g, is scarcely larger than a cigarette package and can for this reason be easily carried.

Figure 3:
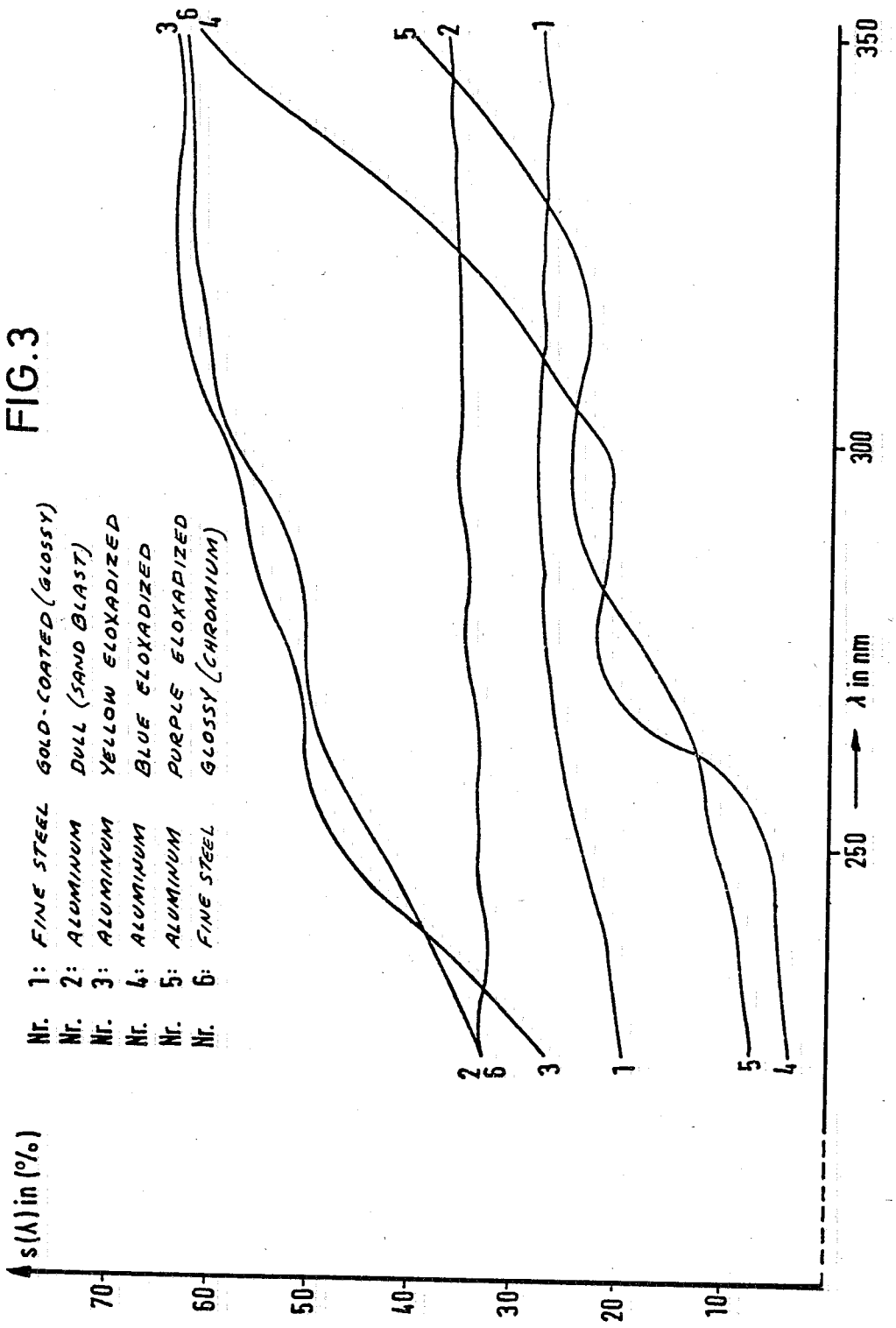
FIG. 3 are various spectrum divisions on reflection of the UV lamp using different reflectors.

FIG. 3 shows the spectral division of the UV radiation emitted for various surface layers of the reflector 34, in which regard the surface layers 3 (aluminum yellow eloxated) and 6 (polished stainless steel (chrome)) are especially preferred.

In order to supply electrical energy to the UV lamp 33 a socket is arranged on the hairdryer 141 into which a plug that is arranged on the mounted sleeve 22 can be inserted when the housing 1 is installed on the hairdryer 141.

Figure 4:
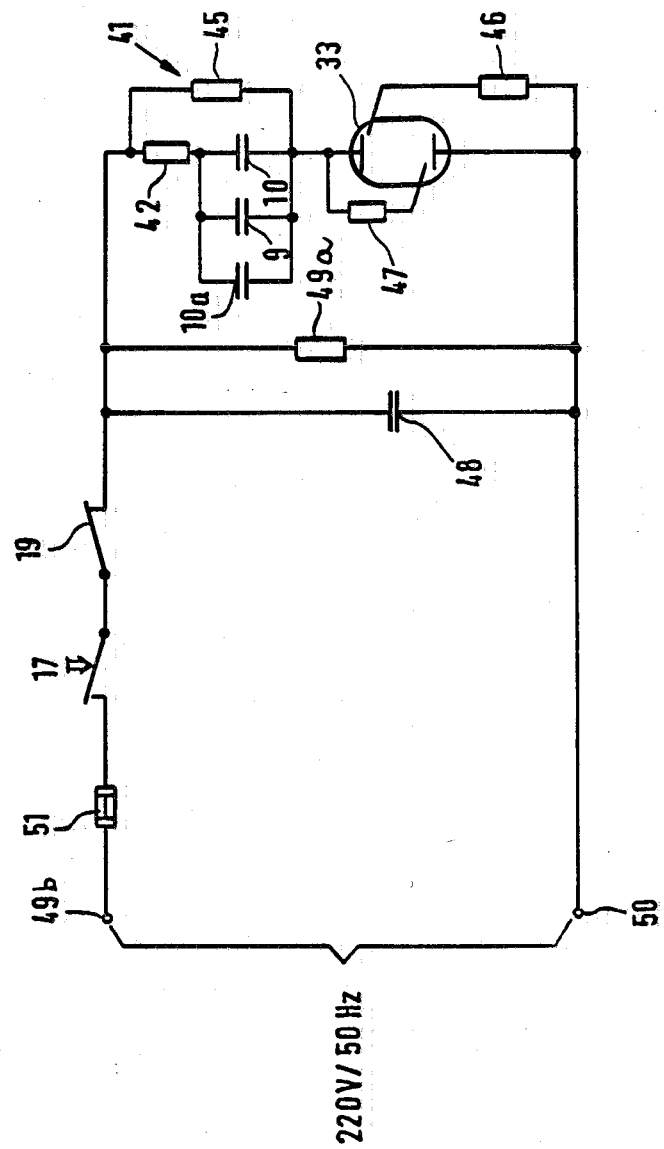
FIG. 4 is the electrical circuit for an ultraviolet lamp, this being according to the invention.
Figure 5:
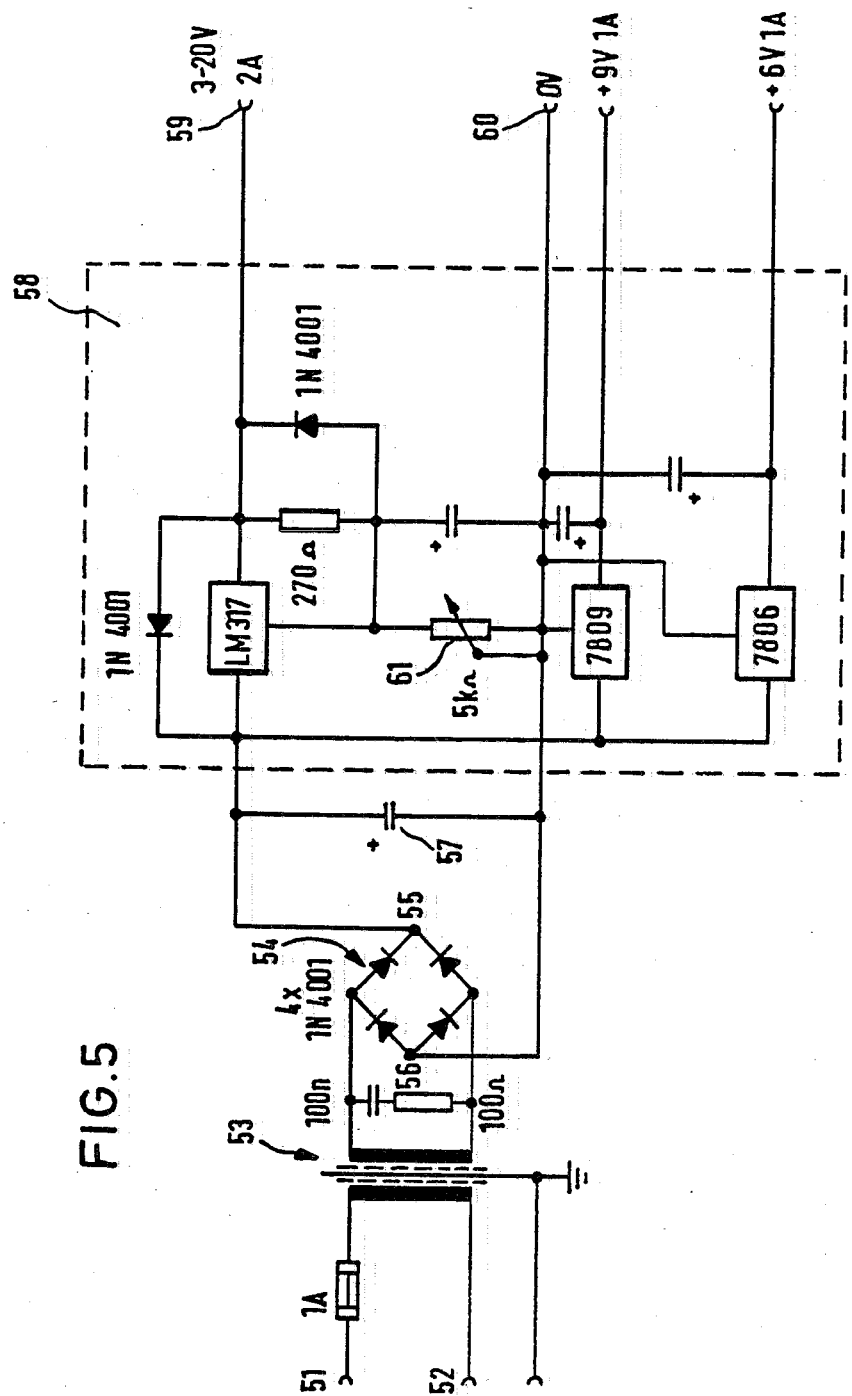
FIG. 5 is a circuit diagram of a power supply unit for a blower.

FIG. 4 shows the electrical circuit for the UV lamp 33. In series with the UV lamp 33 there is a dropping resistor 41 that is made up of DC and capacitive resistors. The dropping resistor 41 consists of a power resistor 42 in series with which there are three condensers 9, 10 and 10a that are connected in parallel. A resistor 45 is connected in parallel to the series circuit consisting of the resistor 42 and the condensers 9, 10 and 10a. If a high pressure mercury vapour lamp OS124 (nominal power consumption 125 W, burner voltage 85 V±11 V and a nominal current of approximately 2 A; made by Osram GmbH) is used as the UV lamp 33 this will require a capacitive dropping resistor for line operation (220 V/50 Hz of 30 μF). Thus the condensers 9, 10 and 10a are each of a capacity of 10 μF. The resistor 42 has a value of 0.5Ω and serves to limit peak current. The resistor 45 serves to discharge the capacitors after the device has been switched off and has a value of approximately 100 KΩ. The UV lamp is triggered through the resistors 46 and 47.

Parallel to the series circuit of the dropping resistor 41 and the UV lamp 33 there is a capacitor 48 as well as a resistor 49a. These components serve to reduce interference. The supply of operating voltage through the terminals 49b and 50 is effected through the series circuit of a fuse (current limiting) 51, the microswitch 17, and the thermoswitch 19.

FIG. 15 shows the power supply unit that is used to supply the motor (DC motor) of the hairdryer 141. Line voltage (220 V/50 Hz) is applied to the input terminals 51 and 52 that is dropped by means of the transformer 53 and then passed to the bridge rectifier 54. There is then a DC voltage at the outputs 55 and 56 of the bridge rectifier 54 that is then smoothed by the condenser 57 and passed to a control and stabilizing circuit 58. The output voltage at the output terminals 59 and 60 can be controlled by means of the potentiometer 61. Since the DC motor of the hairdryer is connected to the output terminals 59 and 60 its rotational speed is adjustable by means of the potentiometer 61, the quantity of air coming from the hairdryer 141 can be controlled. As the operating temperature of the UV lamp is varied its power output will vary, as well as will the wave length of the radiation that is emitted. As has already been described, the quantity of air, and thus the cooling effect exerted on the UV lamp 33, can be controlled at the potentiometer 61. This also provides the possibility of affecting both the power output as well as the wave length of the UV lamp 33. The radiation device according to the present invention can thus be set to optimal adjustment for a particular requirement.

Figure 6:
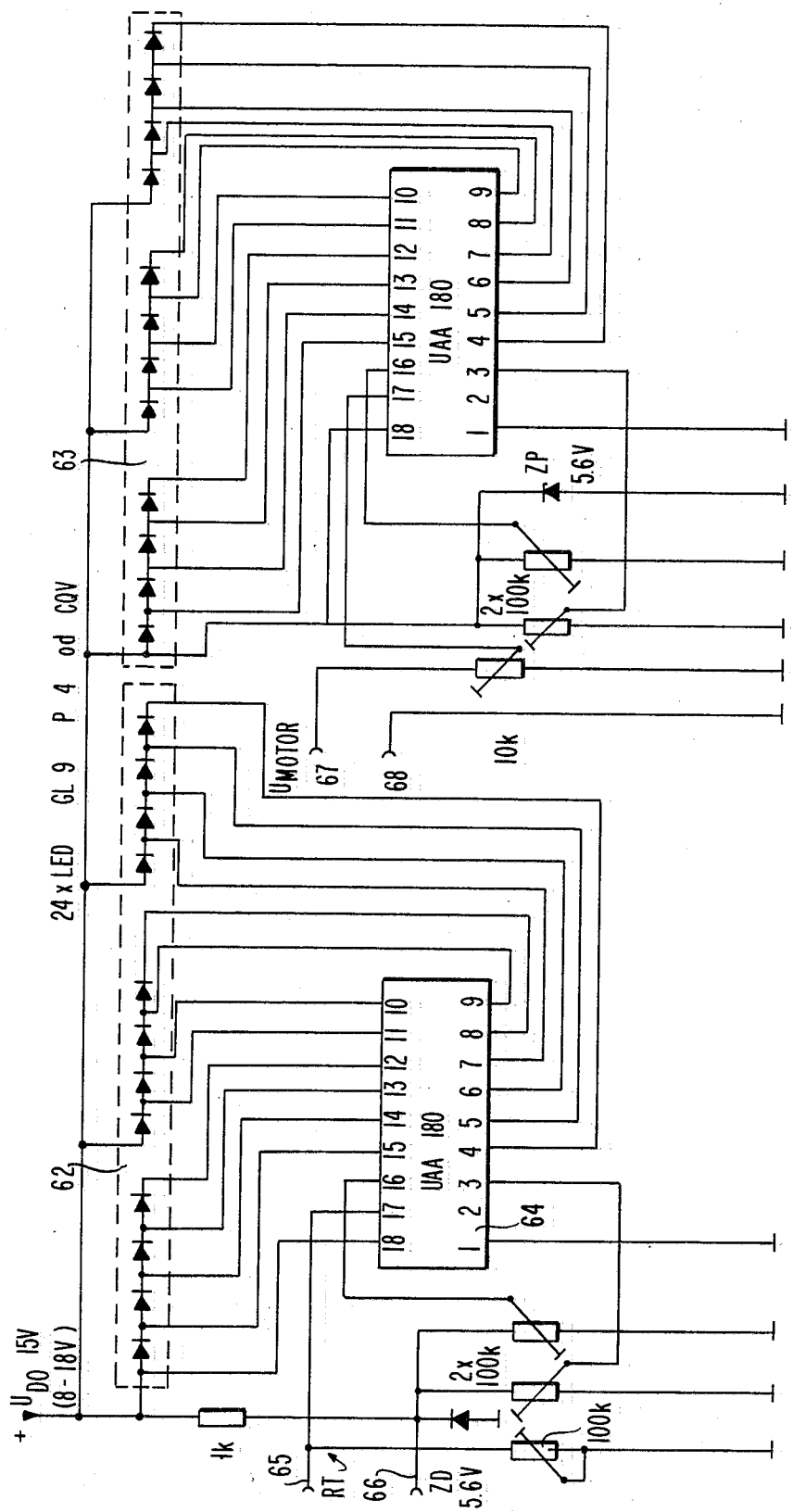
FIG. 6 is an indicator circuit for the operating temperature of the UV lamp as well as for the cooling output of the blower.

FIG. 6 shows an indicator circuit that incorporates two light emitting diodes series 62 and 63. The light emitting diodes series 62 is controlled by the integrated circuit 64 (UAA 180) an is used to indicate the temperature within the radiation device according to the present invention. To this end, a voltage that is proportional to the temperature in the interior 8 of housing 1 is applied to the terminals 65 and 66 and this is then processed in the integrated circuit 64 and a corresponding number of LED's in the LED series 62 is triggered. As an example, an NTC resistor can be used as the temperature sensor. This NTC resistor can be in either direct or indirect contact with the glass bulb of the UV lamp 33, so that the number of LED's that is lit is a function of the temperature of the bulb and thus of the emitted radiation output and the wave length of the radiation emitted by the UV lamp 33. In this regard, the indicator circuit can be such that as the temperature increases so does the number of LED's that is illuminated.

The other series of LED's 63 operates in a similar manner; however, the motor voltage of the hair dryer 141 is passed to it through the terminals 67 and 68, so that the number of LED's that is illuminated in the LED series 63 is a function of the cooling air that is being passed. Thus the person using the device can set the desired operating point of the device according to the present invention by means of the two LED indicators.

Figure 7:
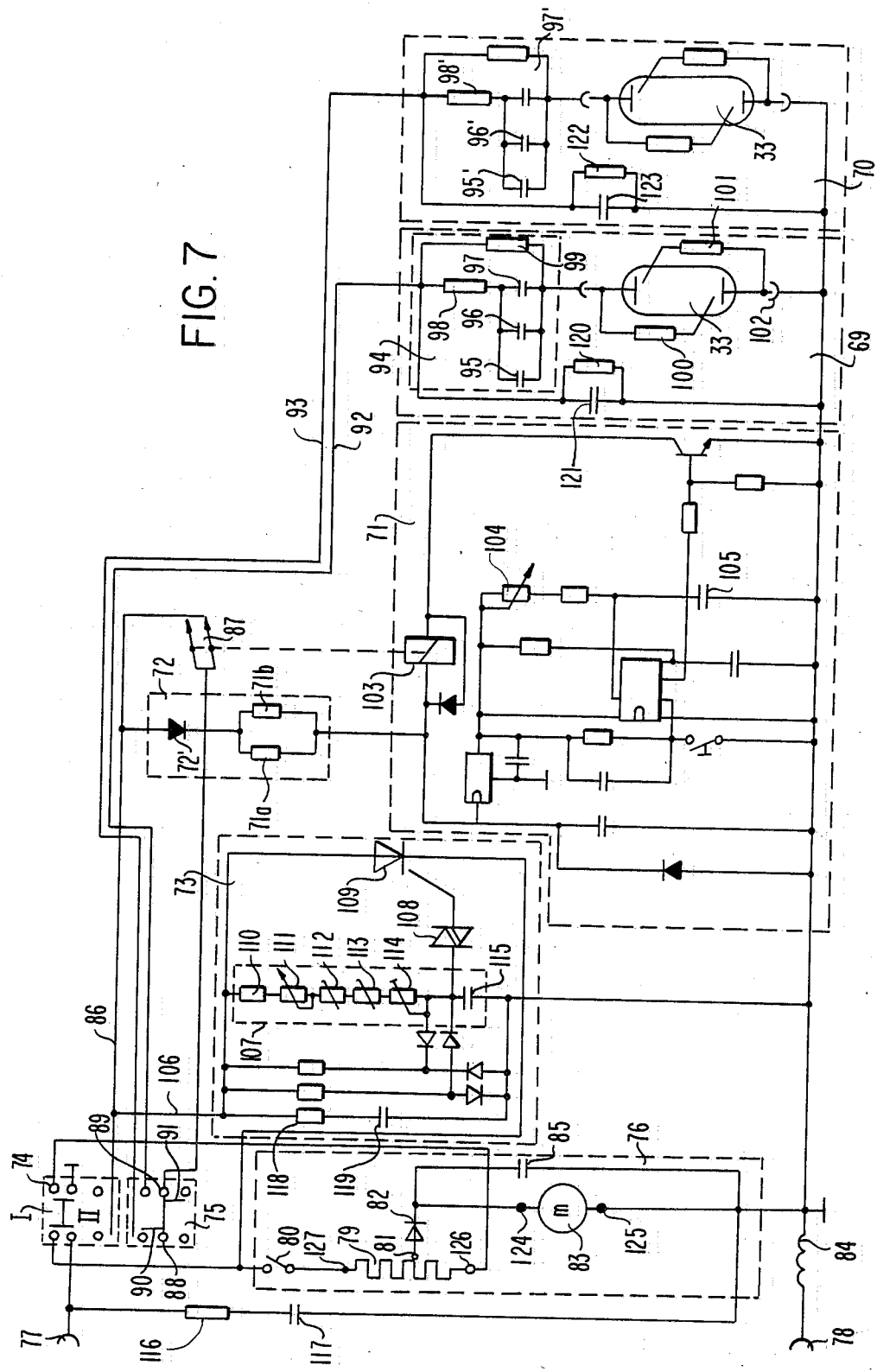
FIG. 7 is an overall circuit diagram for the operation of two UV lamps with controlled cooling.

FIG. 7 is an overall circuit diagram for an irradiation device according to the present invention, in which regard two UV lamps and an automatic cooling air control are provided. The complete circuit consists of two UV lamp circuits 69 and 70, a timer circuit 71, a supply circuit 72 for the timer circuit 71, a phase intersection circuit 73, a hair dryer switch 74, a UV light switch 75, and a hair dryer switch 76.

Figure 8:
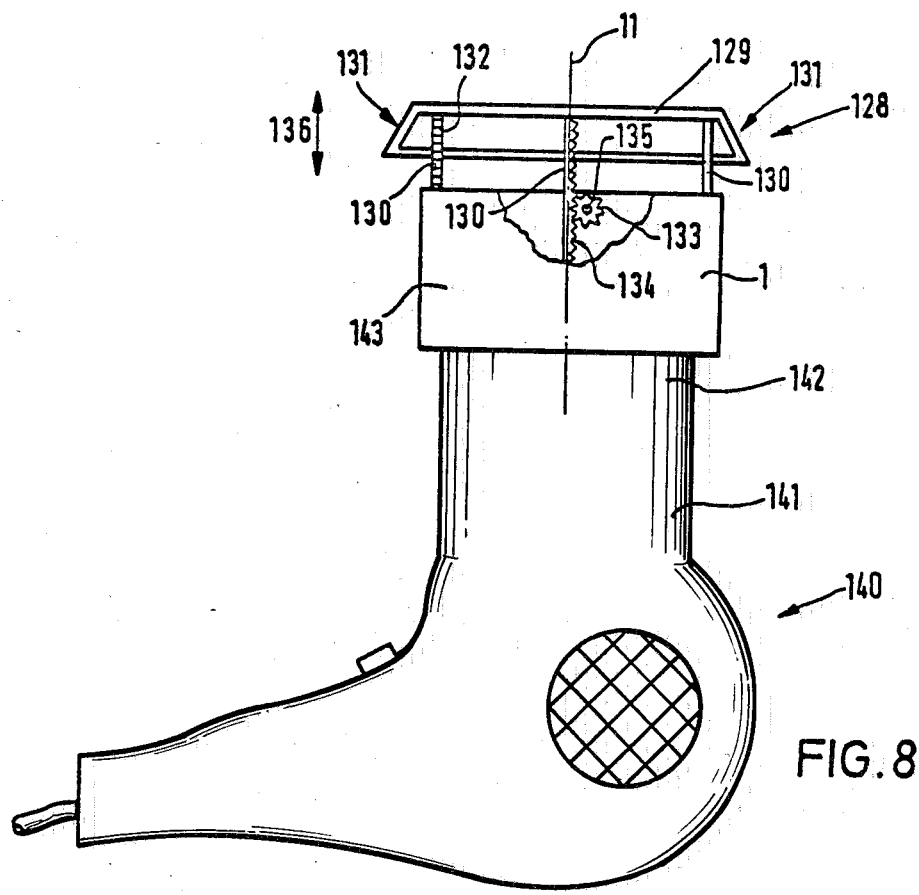
FIG. 8 is a side view of the hair dryer according to the invention with a UV assembly and a distance piece.
Figure 9:
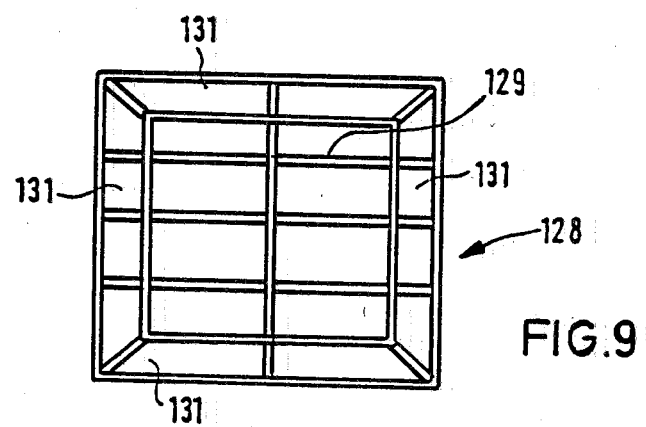
FIG. 9 is a plan view of the distance piece viewed from the object that is to be irradiated.

If line voltage (220 V/50 Hz) is applied to the two terminals 77 and 78 and if the hair dryer switch 74 is in the position I that is shown in FIG. 8, the heater 79 of the hair dryer will be put into operation. The heater 79 is made up of resistance wire that heats up when the current is passed through it. In series with the heater 79 there is a temperature switch 80 that switches off the heater 79 in the event that a preset temperature is exceeded. The heater coil of the heater 79 has a tap 81 to which a diode 82 is connected. One contact 124 of the diode is connected to a DC motor 83; the other pole 125 is connected to the terminal 78 through the choke 84. The DC motor 83 (e.g. a 12 V motor) is the blower motor for the hair dryer. In parallel to the DC motor 83 there is a condenser 85 used to smooth the motor voltage. In this operating state (hair dryer switch 74 in position I) the hair dryer can be used in the conventional manner.

If the hair dryer switch 74 is moved into position II, voltage will be applied to the connections 88 and 89 of the UV lamp switch 75 through the line 86 when the relay contact 87 is closed. According to the position of the switch contacts 90 and 91 the UV lamp circuits 69 and 70 can be switched off or on, respectively, through the lines 92 and 93. The UV lamp circuit 69 consists of a dropping resistor 94, the three condensers 95 to 97 (each of 10 μF) that are connected in parallel, a power resistor 98 (0.5Ω) that is connected in series with these, and a resistor 99 (100 kΩ) that is in parallel to the series circuit of the power resistor 98 and the condenser 97. The UV lamp 33 whose triggering electrodes are in each case connected to the resistors 100 and 101 is in series with the dropping resistor 94. The resistors 100 and 101 are in each case of 15 k and serve to produce the striking voltage. The lower connection 102 in FIG. 7 is connected to the terminal 78 through the choke 84. The three condensers 95, 96 and 97 thus serve as dropping resistors for the UV lamp 33. The resistor 98 limits the peak current and the resistor 99 serves to discharge the condenser after the UV lamp circuit 69 has been switched off. UV lamp circuit 70 is constructed in the same way as UV lamp circuits 69.

The two UV lamp circuits 69 and 70 can only be put into operation if the relay contact 87 is closed. This relay contact is part of the relay 103 of the timer circuit 71. The timing elements of the timing circuit 71 are the potentiometer 104 and the condenser 105. The starting time of the relay 103 can be set on the potentiometer 104. Thus the time that the UV lamp circuits 69 and 70 will be switched on can be determined in the same manner. Since the timer circuit is already familiar from the state of the art, no further details will be provided for the timer circuit 71. The supply circuit 72 for the timer circuit 71 consists of a diode 72' and two power resistors 71a,b that are connected parallel. These are so arranged that they are cooled by the air flow from the hair dryer in order that any heat that they generate can be carried away.

If the hair dryer switch 74 is in position II voltage is applied to the phase intersection circuit 73 through the line 106. The phase intersection circuit 73 has an element 107 that determines the angle of intersection and this controls the diac 108 that is connected to the gate of thyristor 109. When the hair dryer switch 74 is in the operating position that has been described the thyristor 109 is in series with the hair dryer switch 76, in which regard the series circuit of the thyristor 109 and the hair dryer circuit 76 is connected to the operating voltage (220 V/50 Hz) through the choke 84. The supply voltage of the hair dryer can be varied by means of variations in phase intersection angle of the phase intersection circuit 73, this making it possible to change the rotational speed of the DC motor 83. In this manner of operation the supply voltage is applied to the series circuit that is made up of a part of the heater 79 (from the connector 120 of the heater winding to the tap 81), the diode 82, and the motor 83.

The element 107 of the phase intersection circuit 73 that determines the phase intersection angle is formed from the series circuit consisting of the resistor 110, the potentiometer 111, NTC-resistor 112, NTC-resistor 113, trimmer 114, and the condenser 115. The two NTC-resistors 112 and 113 are in each instance associated with a UV lamp circuit 69 or 70, respectively, i.e. each of the two resistors is in the immediate vicinity of the corresponding UV lamp, so that the heat generated by each of the lamps will be registered by the corresponding resistor. The NTC-resistors change their resistance value according to the action of heat, which will change the phase intersection angle of the phase intersection circuit 73 and this in turn will affect the rotational speed of the DC motor 83. With a change in the rotational speed of the motor the quantity of cooling air moved by the hair dryer will also change and in the device according to the invention this is used to cool the UV lamp 33. Subsequently, reference will only be made to one UV lamp although, of course, there can be more, as in FIG. 7, for example, where two UV lamps are used. In describing the control circuit it is understood that the temperature of the UV lamp 33 in UV lamp circuit 69 increases. This causes the NTC-resistor 112 that is located in the immediate vicinity to change temperature and thus change its resistance value. This changes the phase intersection angle of the phase intersection circuit 73 in such a manner that a higher voltage is passed to the hair dryer circuit 76. This increases the rotational speed of the DC motor 83 and a greater quantity of air will be delivered by the hair dryer 141, which will bring about an intensive cooling effect on the UV lamp 33 so that a specific temperature of the UV lamp 33 will be reached. If the temperature of the UV lamp 33 now drops the control circuit will work in the opposite way. The NTC-resistor 113 is associated with the UV lamp circuit 70. The operating point of the radiator can be adjusted precisely at the trimmer 114 of the motor control. The control circuit can be adjusted manually with the help of the potentiometer 111.

Since the circuit according to the invention that is shown in FIG. 7 can generate powerful interference voltages in various places four R-C-combinations (116, 117; 118, 119; 120, 121; 122, 123) as well as the choke 84 are provided to suppress this interference.

When the irradiation device according to the invention is in the automatic operation mode the heat emission from the heater 79 of the hair dryer is of no importance i.e., the varying heat emission of the heater 79 that is associated with the control does not interfere with the maintenance of a specific and preselected operational state. The temperature of the UV lamp 33 can be kept constant, or can be adjusted to a specific value, respectively, with the help of the control circuit shown in FIG. 7 and this temperature can then be kept constant. Since both the radiation power and the emitted wave length of the radiation from UV lamp 33 is dependent on its operating temperature, the desired radiation power and wave length can both be adjusted by adjusting the operating temperature. Thus the optimum operating point of UV lamp 33 for each type of treatment can be set with the help of the treatment device according to the invention. Furthermore, the controlled cooling makes it possible to use the irradiation device for longer periods of operation.

According to a further exemplary version of the invention it is provided that on the housing 1 of the UV assembly 143 there is a distance piece 128 (FIG. 8). The distance piece 128 consists of a flat grid 129 of plastic or wire that is of approximately the size of the side of the UV assembly 143 that faces the object to be irradiated. Stand-off struts 130 are secured to one side of the screen 129 and these are perpendicular to the plane of the screen. These can be displaced in the direction of the longitudinal axis 11 and locked on the housing 1. The edge areas 131 of the screen 129 are angled towards the housing 1. Since it can be moved longitudinally the screen can be adjusted at a preselected distance from the UV lamp 33 of the UV assembly 143. A graduated scale 132 attached to a stand-off strut 130 can if necessary be used to provide precise information regarding the stand-off distance. A pinion 133 that is mounted on the housing 1 in such a manner as to be rotatable engages with a rack 134 on one of the stand-off struts 130. This pinion is made in one piece and coaxially with an operating knob 135 that is arranged outside the housing 1. Manual rotation of the operating knob 135 makes it possible to move the stand-off device 128 in the direction of the double arrow 136. Using the stand-off device 128 the user of the irradiation device according to the present invention can maintain the distance between the area to be treated (e.g. the skin) and the UV lamp 33 very precisely. When this is done the screen 129 is pressed against the area that is to be irradiated. Even in areas that are difficult to reach (e.g., when treating the scalp on the back of the head) the stand-off device 128 is particularly helpful since it makes optimal treatment possible by maintaining the precise irradiation distance.

Figure 10:
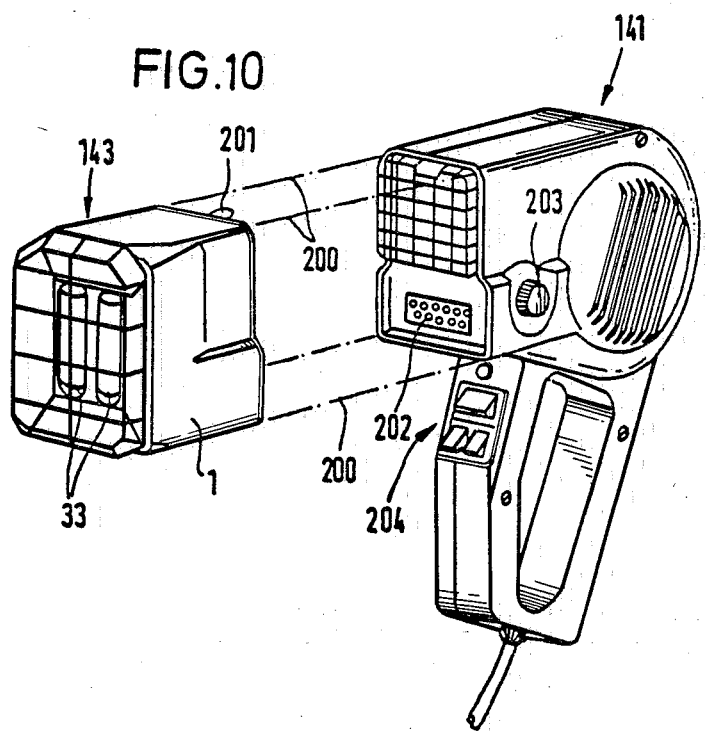
FIG. 10 is a perspective view of a hairdryer according to the invention, this having the UV assembly removed.

FIG. 10 shows a further exemplary version of the irradiation device according to the present invention. In this illustration the hair dryer 141 and the UV assembly 143 are shown separated from each other. The UV assembly 143 can be moved along the dashed lines 200 towards the hair dryer 141 until both parts enter into detent by means of a spring catch 201 that is located in the upper area of the UV assembly 143. When they are in the locked-up position the necessary electrical contacts between the hair dryer 141 and the UV assembly 143 are established by means of a socket 202 arranged on the hair dryer 141 and a corresponding plug, which is not shown in the illustration but which is installed on the UV assembly 143. A knob 203 that is attached to the side of the hair dryer 141 is used to set the irradiation time; this is thus connected with the potentiometer 104 of the timer circuit 71 shown in FIG. 7. The operating elements numbered 204 as a block form a switch for the blower of the hair dryer 141, a switch for the UV lamp 33 that is arranged in the UV assembly 143 and a push button used to start the timer circuit 71 (FIG. 7).

Figure 11:
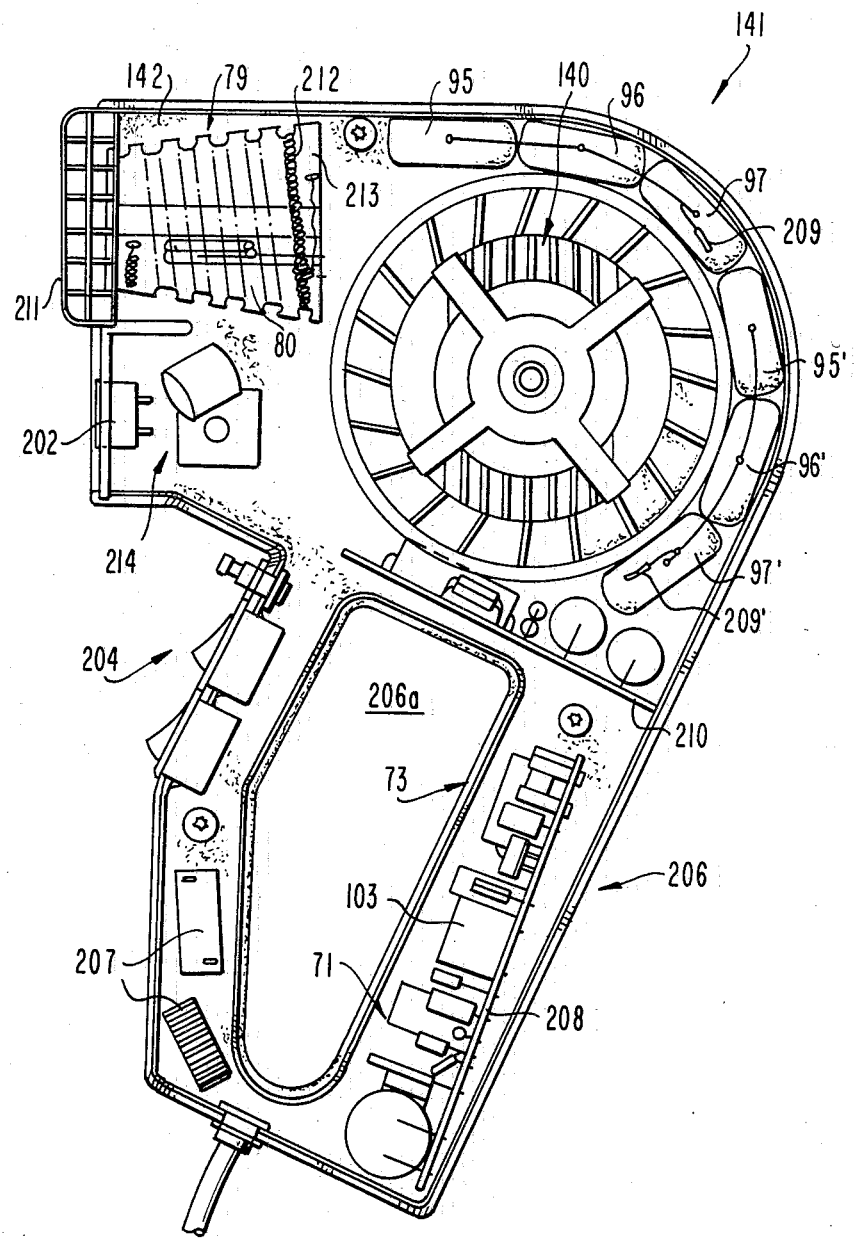
FIG. 11 is a side view of the hairdryer according to FIG. 10 when open.

In FIG. 11, the hair dryer 141 that is shown in FIG. 10 is shown open. A stirrup-like handpiece 206 is integrated into the blower housing 205. As can be seen in FIG. 11, on the left hand upper side this hand grip has the operating elements 204. Beneath this there are constructional elements 207 that are used to suppress interference in the circuits according to the invention that is shown in FIG. 7. In the right hand side of the hand grip 206 there is a circuit board 208 that contains constructional elements and which in its lower area has the timer circuit 71, the relay 103 above this and in the upper area the phase intersection circuit 73. In the head of the dryer 141 there is the blower 140 that is surrounded in a semicircle by the condensers 95, 96 and 97. These condensers form part of the dropping resistor 94 for the UV lamp circuit 69. The three additional condensers 95', 96', and 97' that are connected to the previously mentioned condensers form part of the dropping resistor for the second UV lamp circuit 70. Further constructional elements (resistors that form part of the dropping resistor) are indicated by the reference figures 209 and 209'. Beneath the blower 140 on the circuit board 210 there are the power resistors 98, 98', respectively, of the dropping resistors as well as further interference-eliminating elements of the circuit according to the invention.

The air outlet 142 of the hair dryer 141 is covered by a screen 211 so that any unintentional contact with the heater 79 that is located in this area is prevented. The heater consists of coiled resistance wire 212 that is wound onto a temperature resistant core 213. The temperature switch 80 that is familiar from FIG. 7 is arranged on the core 213.

The socket 202 is secured beneath the air outlet 142; also located here are the components 214 that are filters for the motor.

Figure 12:
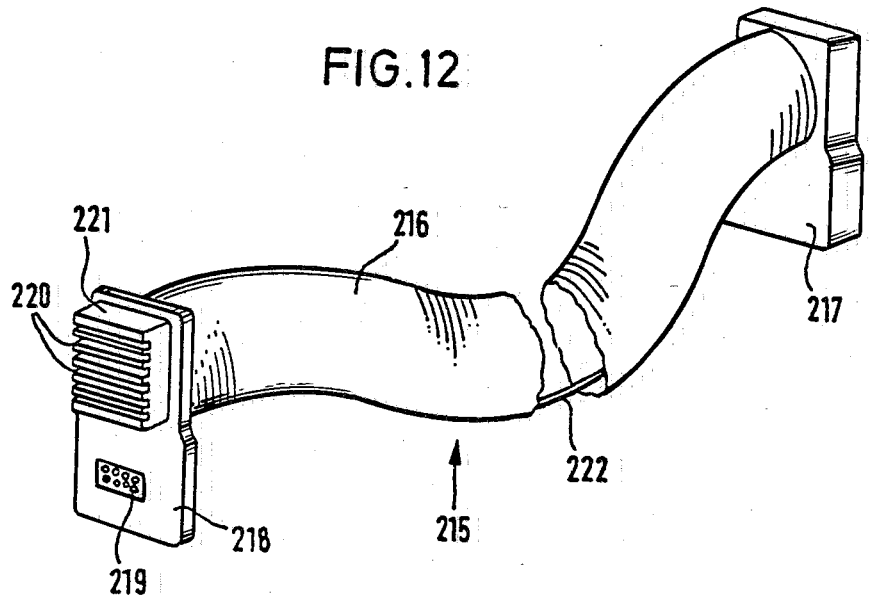
FIG. 12 is a connector device according to the invention, this being used between the UV assembly and the dryer.

According to a further exemplary version of the invention it is foreseen that the UV assembly can be secured to the hair dryer by means of a flexible connector 215 that is shown in FIG. 12. The connector 215 consists of a flexible hose 216 which at one end is connected to a mounting 217 that can be positioned on the air outlets of the hair dryer (not shown in the illustration). At the other end there is a plate 218 which as is shown in FIG. 12, has a socket 219 for the UV assembly 143 in its lower area and this can be positioned on a block 221 that is provided with air outlets 220 and which is connected to the hose 216. The socket 219 is connected to the hair dryer, which is not shown, by means of a supply cable 222 that passes through the flexible hose 216 and other connectors that are not shown in the illustration. This connector assembly 215 makes it possible to arrange the dryer 141 in a holder or similar device and carry out the irradiation treatment by means of the UV assembly 143 that is mounted on the connector assembly 215. In this regard the user need hold only the relatively light UV assembly 143 that is connected to the connector assembly 215; furthermore the flexible hose 216 makes it possible to treat parts of the body that are difficult to reach.

Figure 13:
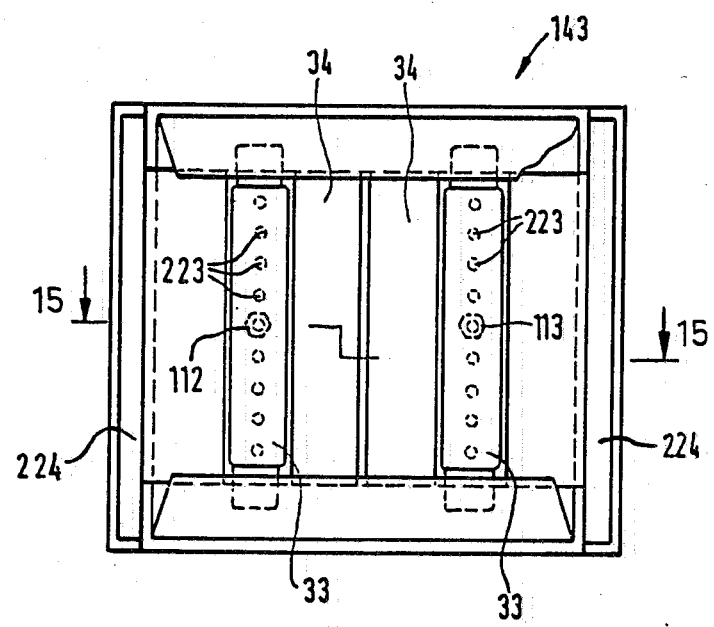
FIG. 13 is a plan view of the front of the UV assembly.

FIG. 13 shows a further exemplary version of the UV assembly 143 according to the present invention viewed from the irradiation side. The front of this UV assembly 143 has two reflectors 34 that are arranged adjacent to each other in the middle of each of which there is a UV lamp 33. Air outlet openings 223 are arranged beneath the UV lamps 33 and part of the stream of air generated by the hair dryer passes through these and thereby cools the UV lamps 33. The air outlet openings 223 extend in each instance over the whole length of the UV lamp 33 and are arranged in a straight line equidistant from each other. On both sides of the front of the UV assembly 143 there is in each instance an air outlet duct 224 that is parallel to the UV lamps 33. When the irradiation device according to the present invention is operated part of the stream of air that is generated by the dryer passes out of these air outlet ducts 224 and this can then be directed by the user to the area that is to be treated.

Figure 14:
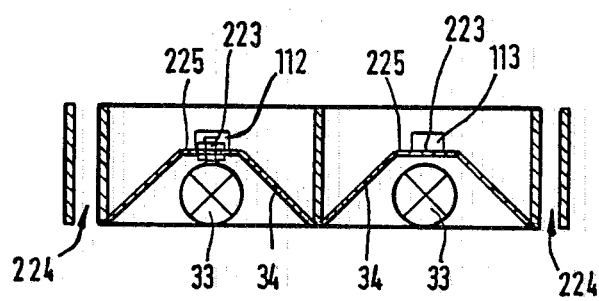
FIG. 14 is a sectional view through the front area of the UV assembly according to the invention according to FIG. 13 along the line 15-16.

FIG. 14 is a cross section through the front area of the UV assembly 143 according to FIG. 13, on the line 15—15. Once again this shows the air outlet openings 223 that are aligned with the UV lamp 33 in each instance. On the side 225 of each of the reflectors 34 that faces the UV lamps 33 there are arranged in the immediate vicinity of the air outlet openings the two NTC-resistors 112, 113, respectively, that are familiar from FIG. 7. These NTC-resistors provide information concerning the temperature of the UV lamps.

The exemplary version shown in FIGS. 10, 11, 13, and 14 of the irradiation device according to the present invention each have two UV lamps 33. In this connection it is expedient to use different UV lamps; thus, for example, one lamp that emits UV-A radiation and one can be used which emits UV-B-A radiation. According to another exemplary version it is however conceivable that the objects shown in FIGS. 10, 11, 13, and 14 each incorporate only one UV lamp.

In the exemplary version shown the UV radiator is in each instance arranged in a block which can be mounted separately on the air outlet. However, the invention relates also to the arrangement of the UV radiator directly on the dryer housing, this being done in the area of the air outlet, in which regard ther remaining electrical circuits used to operate the irradiation device according to the invention and the configuration of the radiator and the management of the flow of air can be managed as described above.

The invention includes all features and versions that are equivalent in the sense of the invention.

The additional device according to the invention shown in FIG. 15 can be used in particular to irradiate specific small objects, particularly parts of the body. It is also possible to reach those parts of the body that are relatively inaccessible by means of a flexible hose 303. The hair dryer that is used to produce the stream of air 302 can be fixed because the source of radiation is arranged at the head end of the flexible hose 303 and the flow of air is directed through the hose 303.

In the main the additional device consists of the duct 301 into which the stream of air 302 from the hair dryer (which is not shown) is introduced trhough the rear opening 304. The temperature of the air as well as the quantity of air are preferably variable. In the area of the front opening 305 of the duct 301 there is at least one source of UV radiation 306 and this is contained in the socket 307. Electrical wires 308 run from the socket 307 to the rear opening 304; here they are supplied with power through the cable with the plug or similar device.

In the direction of flow of the air from the source of radaition 306 there are reflectors 309 and these are preferably provided with holes 310; the air can flow through these holes 310, pass around the source of radiation 306, and then be directed with the radiation to the object.

According to FIG. 16 there are two radiators arranged in the duct 301 and in each instance these are formed by a source of radiation 306 and a reflector 309. To one side and adjacent to one of these radiators there is a container 311. The walls of the container 311 are gas and/or moisture permeable so that the flow of air 302 can flow through these and thereby pick up one or several gaseous or vaporized materials from a product that is in the container 311. To this end the container 311 can preferably have an inside portion that is formed of replaceable mesh-like material in order that the mesh container can be used to insert the material that holds the gas or the vapor that is to be delivered or which emits a gas or vapor in the container 311. The arrows in FIG. 16 indicate the direction of flow of the air 302. As is shown by the continuous arrows, the flow of air 302 passes to the radiators 306, 309 and to the container 311 (see arrow 302a). The air flow 302 passes into container 311 where it is charged with the transportable material, e.g., a perfume or oil or the like, and leaves the container in the direction of the object that is to be treated. Since the adjacent air stream 302 passes around the sources of radiation 306 simultaneously and subsequently flows in the direction of the UV radiators to the object that is to be irradiated this results in a combined effect of UV radiation with an integrated air flow and then integrated air-gas or air-vapor, respectively flow. Thus, in addition to the UV radiation the additional material that was kept in the container 311 also passes to the object in the form of gas or vapor. Familiar means can be provided to change the permeability of the container.

In order to increase the range of application of the device according to the invention it is more expediently provided that the air flow 302 can be deflected in the duct 301. To this end a deflector 312 is arranged in the duct 301 in such a manner as to permit it to pivot, this being done in the direction of flow of the air flow 302 in front of the radiators 306 and the container 311. The deflector 312 is preferably matched to the cross-section of the duct 301 so that it can shut off specific parts of the air flow 302. Thus it is best installed perpendicular to the direction of flow of the air flow 302 in the duct 301 and is installed on the shaft 316 in such a manner as to be able to pivot. Preferably the shaft 316 is located on the forward edge of the deflector 312 at some lateral distance from a side of the housing 301, to one side of the centre (see FIG. 16). Using a handle that is located outside on the housing 301 which is connected to the shaft 316, this handle being in the form of a knob, the deflector 312 can be pivoted about the shaft 316. The deflector 312 is preferably long enough that it can be swung against both the left and the right walls (FIG. 16). If it is desired, for example, to prevent the air flow 302 from passing by the container 311 and the radiators 306, 309, the deflector 312 is moved from the position shown by the continuous lines into the position shown by the dashed lines. The device then works as a UV radiator with the air flow emerging from the side of the device and this can be most expediently directed by a familiar means directly onto the object that is to be irradiated. Since in this case the air flow 302 cannot reach the container 311, the function of the container 311 is inoperative.

The function of the device according the present invention is most expediently extended by a further deflector 312a that is mounted in such a manner as to be able to pivot in the duct 301. This deflector 312a is preferably also matched to the cross section of the duct 301 and is arranged so as to be able to pivot about the shaft 314 that is parallel to the shaft 316 and is loacted in the side wall area of the duct 301 ahead of the container 311. It is considerably shorter than the deflector 312 and is simply long enough that when it is in the position indicated by the dashed line it can shield the container 311 from the flow of air 302 in such a manner that the container 311 is protected from the flow of air. To this end an additional deflector wall 324 can be arranged in the direction of flow between the container 311 and the adjacent radiator 306, 309 against which the deflector 312a can be pivoted so as to provide a better sealing of the container 311 against the air flow 302. The deflector 312a is best mounted in the same way as the deflector 312, in which connection a shaft is connected to a control that is located on the outside of the housing 301. If it is desired to prevent the air flow 302 reaching the container 311 the deflector 312 is pivoted in front of the container 311 in such a way that the air flow 302 is deflected by the deflector 312a in the direction of the radiators 306, 309.

According to a further version of the invention a partition 318 extends from the shaft 316 to the opening 304 of the duct 301 so that a partial duct 322 is formed. This partial duct 322 works in conjunction with the deflector 312 and prevents the air flow 302 from reaching the radiators 306, 309 if the deflector 312 has been pivoted into the position shown by the dashed lines. It can be expedient to configure the partition 318 in such a manner that the air flow 302 is deflected completely from the object that is to be irradiated.

Within the framework of this invention it is possible to implement a process in which the UV radiation, and in particular its intensity, is changed, in that the source of radiation is arranged in an area of a gas and is rinsed by the gas. When this is done a flow of gas is directed to the source of radiation and this forms a type of gas cushion or gas cloud in front of the source of radiation. The gas flow can be deflected in the direction of the UV radiation as a directed gas jet, in which connection a rinse gas can be used for the gas flow. The rinse gas can in particular be air. It is advantageous if the gas rinses and/or the gas flows are periodically combined with UV radiation and if in front of the source of radiation a gas build up that is of greater static pressure than the outside atmosphere is built up with the rinse gas. It can be expedient to change the type of gas or use different gases for the rinse gas and the gas flow. The quantity of gas as well as the static pressure and the dynamic pressure of the gas jet can also be varied expediently. It is also expedient to use gases at different temperatures. It was surprising that because of the fact that a flowing gas was brought into the path of the radiation between the source of radiation and the object to be irradiated and if in addition the gas was directed onto the object in the form of a gas jet this being in the direction of the UV radiation it was possible to achieve an effect that was previously unknown. It was shown that the effect of the radiation was changed. For example, the healing achieved in skin disorders is considerably better; there was a more rapid alleviation, for example, of psoriasis, if air was used for the washing and for the gas jet; however, other skin disorders were healed more rapidly as well. The reason for this changed effect of the radiation from a source of radiation has not as yet been determined. Possibly the composition of the gas mixture changes and/or the quantity of gas that is delivered per unit time to the object promotes this and/or the filter effect of the washed gas and/or of the gas for the gas jet causes this surprising effect. A favourable effect can then be achieved if a flowing gas is passed through the path of the radiation between the source of radiation and the object that is to be irradiated. The gas flow can be perpendicular to the direction of irradiation or can be directed at an angle to the direction of radiation. The invention foresees that the type of gas, the quantity of gas, the direction of gas flow, the gas temperature and the static and dynamic pressure of the gas are all variable. It can be expedient to direct the gas in layers perpendicular or inclined through the space between the source of radiation and the object that is to be irradiated, in which connection in like manner, in particular the thickness of the layer, the speed of the flow, the type of gas and the gas temperature are all directed towards the desired change in the radiation. In comination with the possibilities of changing the radiation according to the invention familiar possibilities for modification such as, for example, radiation sources that can be switched on on or off and/or filters can be used. In the case of large area radiators such as sunlamps the invention can also be used to effect in that gas flows are produced by zones in the radiator, this being done in the areas in which the object that is to irradiated is to be treated with radiation of varying intensities.

The embodiments of the invention in which an exclusive property or privilege is claimed are defined as follows:

1. An irradiation device comprising in combination a blower, a source of radiation that emits ultraviolet radiation and is connected through a voltage-dropping impedance to an AC power source, the radiation source being operable in conjunction with the flow of air produced by the blower, the voltage-dropping impedance being capacitive, the source of radiation (33) being arranged in the air flow from the blower (140), means for determining a temperature of the source of radiation at a predetermined operating point; and means for controlling the air flow of the blower upon a temperature increase or a temperature reduction of the source of radiation for cooling the source of radiation in dependence from a temperature change in such a manner that the instantaneous value of the restriking voltage is less than or equal to the instantaneous value of the line voltage.

2. An irradiation device according to claim 1, wherein the blower (140) is a hair dryer (141) having an air outlet (142) with a housing (1) mounted and locked thereon, said housing containing the source of radiation (33) and the voltage-dropping impedance (41,94).

3. An irradiation device according to claim 2, further including a mounting (22) fitted onto the air outlet (142) of the blower (141).

4. An irradiation device according to claim 3, wherein said voltage dropping impedance includes condensers (9, 10; 95, 96, 97) and air channels (24, 25) are formed in the housing (1), said channels starting from an opening (23) of the mounting (22) along the air flow past the condensers (9, 10; 95, 96, 97) of the capacitive voltage-dropping impedance (41, 94) and to the source of UV radiation (33) and a socket (30) for the source of UV radiation (33).

5. An irradiation device according to claim 4, wherein outlets (26,27,28,29) for the removal of the cooling air are provided in the housing (1).

6. An irradiation device according to to claim 5, wherein a reflector (34) has several flat surfaces (35, 36, 37, 38, 39).

7. An irradiation device according to claim 6, wherein the flat surfaces (35, 36, 37, 38, 39) are selectively arranged at an angle to each other and a main direction of reflection thereof is directed approximately onto a delimited radiation surface.

8. An irradiation device according to claim 6, characterized in that the reflector (34) is of plastic.

9. An irradiation device according to claim 6, wherein the surfaces of the reflector (34) are metal coated.

10. An irradiation device according to claim 9, wherein a surface layer is of stainless steel and/or of chromium.

11. An irradiation device according to claim 9, wherein a surface layer consists of yellow anodized aluminum.

12. An irradiation device according to claim 5, wherein the reflector (34) has a surface layer that reflects UV-A radiation.

13. An irradiation device according to claim 5, wherein the reflector (34) has cooling air outlet openings (223) to supply cooling air from the blower to the source of radiation (33).

14. An irradiation device according to claim 5, wherein the source of radiation (33) is a high pressure mercury vapour lamp (33).

15. An irradiation device according to claim 14, wherein a UV lamp (33), that emits a high proportion of long wave UV-A radiation is used.

16. An irradiation device according to claim 15, wherein the spectrum of the emitted radiation of the UV lamp (33) is in the wave length range of approximately 240 nm to approximately 585 nm.

17. An irradiation device according to claim 15, wherein a filter system is arranged in the path of the radiation of the irradiation device, said system suppressing short wave UV-B and UV-C radiation.

18. An irradiation device according to claim 15, wherein a filter device that suppresses long wave visible radiation and IR radiation is provided.

19. An irradiation device according to claim 3, wherein the capacitive voltage-dropping impedance (41, 94) has at least one condenser (9, 10; 95, 96, 97) that is incorporated in series to the UV lamp (33).

20. An irradiation device according to claim 19, wherein the capacitive dropping impedance (41, 94) has several condensers (9, 10; 95, 96, 97) connected in parallel to each other.

21. An irradiation device according to claim 20, wherein a discharge resistor (45, 99) is provided that is connected in parallel to the condensor (9, 10; 95, 96, 97).

22. An irradiation device according to claim 21, wherein the voltage-dropping impedance (41, 94) has a resistor (42, 98) used to eliminate voltage peaks, said resistor being connected in series to the the condensers, respectively (9, 10; 95, 96, 97).

23. An irradiation device according to claim 22, wherein the discharge resistor (45, 99) is connected in paallel to a series circuit consisting of a voltage peak limited resistance (42, 98) and the condensers, respectively, (9, 10; 95, 96, 97).

24. An irradiation device according to claim 5, wherein the hair dryer (141) has a motor (83) and a heater coil (79), in which in a first operating mode of the hair dryer (141) the heater coil (79) is supplied with operating voltage and the motor (83) is connected to a part section of the heater coil (79).

25. An irradiation device according to claim 24, wherein one motor connector (124) is connected to a tap (81) of the heater coil (79), the other motor connector (125) being connected to one end (126) of the heater coil (79).

26. An irradiation device according to claim 24, wherein the hair dryer (141 is operated so that at least a part of the heater coil (79) is used as a dropping resistor for the motor (83).

27. An irradiation device according to claim 26, wherein the motor connector (24) is connected to the tap (81) of the heater coil (79) that serves as a dropping resistor and the supply voltage for the hair dryer (141) is applied between the other motor connector (125) and a start (127) of the heater coil (79).

28. An irradiation device according to claim 25, wherein the motor is a DC motor (83) and is connected to the tap (81) of the heater coil (79) through a diode (82).

29. An irradiation device according to claim 26, wherein a thyristor (109) of a phase intersection circuit (73) is connected in series to the heater coil (79), the phase intersection circuit (73) being used to control the rotational speed of the motor (83).

30. An irradiation device according to claim 29, wherein an element (107) of the phase intersection circuit (73) for determining a phase intersection angle has at least one NTC-resistance (112, 113) arranged in the immediate vicinity of the UV lamp (33) in order to determine its temperature.

31. An irradiation device according to claim 30, wherein the element (107) for determining the phase intersection angle consists of several NTC-resistors, which are associated with the UV lamp.

32. An irradiation device according to claim 30, wherein a motor speed adjustment trimmer (114) is used to adjust an operating point (temperature adjustment) of the UV lamp, said trimmer being connected in series to the NTC-resistors, respectively, (112, 113).

33. An irradiation device according to claim 30, wherein the speed of the motor in the hair dryer is controlled by means of the phase intersection circuit (73) in such a manner that the UV lamp is maintained at a constant preselected temperature.

34. An irradiation device according to claim 30, wherein a timer circuit (71) is used to switch the UV lamp on or off so as to provide for a precise measurement of the radiation dose.

35. An irradiation device according to claim 1 wherein the blower (140) is a hair dryer (141) in an air outlet (142) of which the source of radiation is arranged, the voltage-dropping impedance (41, 94) being arranged and distributed within the blower housing.

36. An irradiation device according to claim 15, wherein a flexible hose (216) with a mounting (217) is installed on the air outlet of the hair dryer, the mounting being provided with air outlet slits (220) secured to the end of the flexible hose opposite the mounting, the hose being used to connect a UV attachment (143) which has the source of radiation.

37. An irradiation device according to claim 36, wherein an electrical connection line is integrated in the flexible hose (216), said line connecting the hair dryer (141) with the UV attachment (143).

38. An irradiation device according to claim 37, wherein an air outlet area of the UV radiator is formed at air outlet openings (223) which are arranged in the direction of flow seen from the UV lamp (33) and are distributed over the whole length of the lamp and air outlet ducts (224) being formed at both sides of the UV lamp opposite each other and parallel to the UV lamp.

39. An irradiation device according to claim 38, wherein a stirrup-like hand grip (206) is provided, which is integral with the housing of the hair dryer (205), the housing having a central opening (206a), whereby a favourable distribution of weight and proper distribution of the individual components in the grip result.

40. An irradiation device according to claim 39, wherein beneath the air outlet in the housing a connector plug (202) is provided for the electrical connection of the irradiation attachment.

41. An irradiation device according to claim 39, wherein said housing has a gas channel (301) with a rear opening (304) and an outlet (305), at least one replaceable radiation source (306) being arranged at said outlet in such a manner that its radiation leaves the outlet (305) to the front, the rear opening (304) of the gas channel (301) being connected with a device that produces a gas flow and which is if necessary connected to a gas source, the gas flow being forced into the gas channel (301) and the source of radiation (306) being so positioned that it is washed by the gas and the gas flow can accordingly leave the outlet (305) as a directed gas jet.

42. An irradiation device according to claim 41, wherein the source of radiation (306) is held in sockets (307) which have electrical elements which supply the source of radiation (306) with electrical energy, and wherein electrical lines (308) are provided, which lead from the socket (307) to the rear opening (304) and to a plug element, where they are arranged so as to be connectable to the other electrical plugs and switching elements.

43. An irradiation device according to claim 42, wherein behind the radiation source (306) a reflector (309) is arranged, said reflector having holes (310).

44. An irradiation device according to claim 43, wherein the size of the holes (310) can be changed, said holes being closeable.

45. An irradiation device according to one or several of claim 43, wherein a blocking plate (311) of material that permits the passage of UV radiation is arranged in front of the radiation source (306) in the outlet (305) of the gas channel (301).

46. An irradiation device according to cliam 45, wherein the blocking plate (311) consists of filter material for specific wave length ranges of UV radiation.

47. An irradiation device according to claim 45 wherein between the blocking plate (311) and the reflector (309) at least one gap (312) is provided.

48. An irradiation device according to claim 45, wherein the blocking plate (311) is arranged so as to be replaceable in the area of the outlet (305) in the gas channel (301).

49. An irradiation device according to claim 48, wherein means to vary the gas pressure of the in-flowing gases (302) and its temperature are provided.

50. An irradiation device according to claim 49, wherein a metal shield (313) is in each instance arranged ahead of the sockets (307) in order to protect the sockets (307) in the outlet opening (305).

51. An irradiation device according to claim 50, wherein the rear opening (304) and the gas source, respectively, are connected to each other by means of a flexible hose (303).

52. An irradiation device according to claim 51, wherein a radiator (315) of a large area sunlamp (314) is provided, having several radiation sources (306) surrounded by reflectors (309) and gas lines (316) are provided, the gas lines being connected to the gas channels (301), which surround the reflectors and the sources of radiation (306) so that a gas flow (317) can be formed which is substantially parallel to the radiation (318) of the source of radiation (306) in each instance.

53. An irradiation device according to claim 52, wherein the reflectors (309) have gas flow openings (310).

54. An irradiation device according to claim 52, wherein a plurality of the radiation sources (306) are provided with gas channels (301) of which at least one is arranged so as to be closeable to cease the supply of gas.

55. An irradiation device according to claim 54, wherein at least one deflector (312) is pivotally arranged in the channel (301) in front of the radiator (306, 309) for at least partially deflecting the air flow (302).

56. An irradiation device according to claim 55, wherein a container (311) is arranged to one side of and adjacent to the radiator (306, 309), said container having walls which are gas and/or vapour permeable.

57. An irradiation device according to claim 55, wherein the channel (301) into which the air flow (302) from the hair dryer can be introduced through the rear opening (304) and in the area of the front opening (305) of the channel (301) at least one source of UV radiation (306) is positioned, which is held in the sockets (307, and the electrical lines (308) running from the sockets (307) to the rear opening (304), and in the direction of flow of the air reflectors (309) being installed in front of the source of radiation (306), the air reflectors being provided with holes, so that air can flow through the holes (310) and wash over the sources of radiation (306).

58. An irradiation device according to claim 57, wherein the container (311) is acted on by the air flow (302).

59. An irradiation device according to claim 58, wherein the container (311) has an inner portion configured as a replaceable mesh insert.

60. An irradiation device according to claim 59, wherein the deflector (312) is arranged in the channel (301) in front of the UV radiators (306) and the container (311), the deflector (312) having a cross-section matched to the cross-section outline of the channel (301).

61. An irradiation device according to claim 60, wherein the deflector (312) is installed in such a manner as to be able to pivot about a shaft (316) perpendicular to the direction of the air flow (302) in the channel (301).

62. An irradiation device according to claim 61, wherein the shaft (316) is positioned at a front edge of the deflector (312) and is laterally spaced from a wall of the housing (311).

63. An irradiation device according to claim 62, wherein the deflector (312) is of such a length that it can be pivoted to rest against both a left-hand and also against a right-hand wall of the housing (301).

64. An irradiation device according to claim 63, wherein a further deflector (312a) is arranged in the channel (301), said further deflector being pivotable and having a cross-section matched to the cross-section of the channel (301) and which is arranged so as to be able to pivot about a further shaft (314) and which is located in a side wall area of the channel (301) in front of the container (311).

65. An irradiation device according to claim 64, wherein a fixed partition (324) is arranged between the container (311) and an adjacent radiator (306, 309).

66. An irradiation device according to claim 65, wherein a further fixed partition (318) extends from the shaft (316) to the opening (304) of the channel (301).

67. An irradiation device according to claim 37, wherein a stand-off device (128) is secured to the housing (1,301) of the UV attachment (143).

68. In irradiation device according to claim 67, wherein the stand-off device (128) consists of a grid (129) of plastic, which is of a size of the side of the UV attachment (143) and is faced towards an object to be irradiated, said stand-off device including stand-off struts (130) secured at one end to a screen (129), said struts being at right angles to the plane of the screen and at the other end, in the direction of a longitudinal axis (11) of the housing, said struts being arranged so as to be displaceable and lockable on the housing (1).

69. An irradiation device according to claim 68, characterized in that the edge areas (131) of the screen (129) are angled down in the direction of the housing (1).

70. An irradiation device according to claim 69, wherein a graduated scale (132) is disposed on one stand-off strut (130).

71. An irradiation device according to claim 70, wherein a pinion (133) is mounted on the housing (1) so as to be rotatable, said pinion engaging with a rack (134) mounted on one of the stand-off struts (130), the pinion being connected to an operating knob (135) which is arranged outside the housing (1).

* * * * *